United States Patent
Nagasaki et al.

(10) Patent No.: US 10,185,395 B2
(45) Date of Patent: Jan. 22, 2019

(54) INPUT DEVICE, INFORMATION PROCESSING DEVICE, AND INPUT METHOD

(71) Applicant: Seiko Epson Corporation, Tokyo (JP)

(72) Inventors: Shintaro Nagasaki, Hara-mura (JP); Yuichi Takano, Matsumoto (JP)

(73) Assignee: Seiko Epson Corporation, Tokyo (JP)

( * ) Notice: Subject to any disclaimer, the term of this patent is extended or adjusted under 35 U.S.C. 154(b) by 0 days.

(21) Appl. No.: 14/998,290

(22) Filed: Dec. 24, 2015

(65) Prior Publication Data

US 2016/0139667 A1 May 19, 2016

Related U.S. Application Data

(63) Continuation of application No. PCT/JP2014/003368, filed on Jun. 23, 2014.

(30) Foreign Application Priority Data

Jun. 26, 2013 (JP) .................................. 2013-133473

(51) Int. Cl.

| G06F 3/01 | (2006.01) |
|---|---|
| A61B 5/00 | (2006.01) |
| A61B 5/021 | (2006.01) |
| A61B 5/024 | (2006.01) |
| A61B 5/11 | (2006.01) |
| A61B 5/0205 | (2006.01) |

(Continued)

(52) U.S. Cl.
CPC ............ *G06F 3/014* (2013.01); *A61B 5/0205* (2013.01); *A61B 5/02108* (2013.01); *A61B 5/02427* (2013.01); *A61B 5/1122* (2013.01); *A61B 5/681* (2013.01); *A61B 5/7445* (2013.01); *A61B 5/7475* (2013.01); *G06F 1/163* (2013.01); *G06F 3/017* (2013.01); *G06F 3/0346* (2013.01)

(58) Field of Classification Search
CPC .............. A61B 5/7475; A61B 5/02108; A61B 5/02427; A61B 5/1122; A61B 5/681; A61B 5/0205; A61B 5/7445; G06F 1/163; G06F 3/0346; G06F 3/014; G06F 3/017
See application file for complete search history.

(56) References Cited

U.S. PATENT DOCUMENTS

| 2006/0028429 A1* | 2/2006 | Kanevsky ............... G06F 3/017 345/156 |
|---|---|---|
| 2010/0156676 A1 | 6/2010 | Mooring et al. |

(Continued)

FOREIGN PATENT DOCUMENTS

| JP | 10-240434 A | 9/1998 |
|---|---|---|
| JP | 2012-075489 A | 4/2012 |
| JP | 2014-174902 A | 9/2014 |

*Primary Examiner* — Christopher E Leiby
(74) *Attorney, Agent, or Firm* — Kilpatrick Townsend & Stockton LLP

(57) ABSTRACT

To provide a device that efficiently selects desired data out of a large number of selectable data.

A pulse meter 10 includes a body motion sensor 60 that detects body motion information concerning a limb, an inclination-angle calculating unit 24 that calculates an inclination angle of the limb on the basis of the body motion information, a display unit 50 that displays an input candidate value corresponding to the inclination angle, and a determination instructing unit 40 that decides the input candidate value as an input value.

11 Claims, 5 Drawing Sheets

(51) Int. Cl.
*G06F 3/0346* (2013.01)
*G06F 1/16* (2006.01)

(56) References Cited

U.S. PATENT DOCUMENTS

| | | | |
|---|---|---|---|
| 2012/0040759 A1* | 2/2012 | Ito | A63F 13/428 |
| | | | 463/37 |
| 2012/0083671 A1 | 4/2012 | Kato et al. | |
| 2012/0242626 A1* | 9/2012 | Hu | G06F 3/04897 |
| | | | 345/184 |
| 2014/0244505 A1* | 8/2014 | Kim | G06F 3/014 |
| | | | 705/44 |

* cited by examiner

INPUT DEVICE, INFORMATION PROCESSING DEVICE, AND INPUT METHOD

CROSS-REFERENCES TO RELATED APPLICATIONS

This application is a continuation of PCT Application PCT/JP2014/003368, filed Jun. 23, 2014, which claims priority to Japanese Patent Application No. 2013-133473, filed Jun. 26, 2013, the entireties of which are hereby incorporated by reference.

BACKGROUND

Technical Field

The present invention relates to an input device, an information processing device, and an input method.

Background Art

There is known a detecting device that is worn on a wrist of a subject in a form like a wristwatch and detects biological information such as a pulse and a blood pressure of the subject. When using the detecting device, the subject needs to input individual information such as age and sex necessary for calculating the biological information. These kinds of individual information include a plurality of items. In addition, choices in each of the items are diversified. Therefore, input operation of the individual information is complicated. In recent years, operability and designability are requested for an input unit for inputting the individual information. In a processing device described in PTL 1, operation buttons for inputting individual information are configured by a touch panel to realize visual operation by fingers and sophisticated design.

CITATION LIST

Patent Literature

PTL 1: JP-A-2012-75489

SUMMARY OF INVENTION

Technical Problem

However, since the touch panel is expensive compared with a conventional contact type button, manufacturing costs of the detecting device increase. Further, since a display unit and an operation unit are integrated, the disposition of the touch panel is restricted because of visibility and operability. The size and the disposition of a display region are limited. When desired numerical data is selected out of numerical data including a large number of choices, there is a problem in that operation for operating the touch panel with fingers to extract the desired numerical data out of a large number of numerical data and selecting the extracted numerical data is complicated.

Therefore, the present invention has been devised in view of the problems and it is an object of the present invention to efficiently select desired data out of a large number of selectable data.

Solution to Problem

The present invention has been devised in order to solve at least a part of the problems and can be realized as the following forms or application examples.

APPLICATION EXAMPLE 1

An input device according to this application example includes: a body-motion-information detecting unit configured to detect body motion information concerning a limb; an inclination-angle calculating unit configured to calculate an inclination angle of the limb on the basis of the body motion information; a display unit configured to display an input candidate value corresponding to the inclination angle; and a deciding unit configured to decide the input candidate value as an input value.

With such a configuration, the input device detects the body motion information of the limb, calculates the inclination angle from the detected body motion information, and displays the input candidate value according to the calculated inclination angle. Therefore, since the input candidate value is displayed according to the inclination angle, by inclining the input device while visually recognizing the input candidate value, it is possible to easily and quickly display a desired input candidate value and decide the desired input candidate value as the input value. Therefore, it is possible to efficiently select desired data out of a large number of selectable data.

APPLICATION EXAMPLE 2

In the input device according to the application example, it is preferable that the body-motion-information detecting unit includes an acceleration sensor configured to output an acceleration signal, and the inclination-angle calculating unit calculates a displacement amount from the inclination angle in a predetermined posture of the limb on the basis of the acceleration signal.

With such a configuration, the inclination angle is calculated on the basis of the acceleration signal detected by the acceleration sensor. Therefore, it is possible to easily and inexpensively configure the input device.

APPLICATION EXAMPLE 3

In the input device according to the application example, it is preferable that the input device further includes: a storing unit configured to store the input candidate value in the predetermined posture as a reference value; and a candidate-value determining unit configured to determine an input candidate value to be displayed on the display unit, and the candidate-value determining unit determines an increase/decrease value on the basis of the inclination angle and calculates the input candidate value using the reference value and the increase/decrease value.

With such a configuration, it is possible to display the reference value as the input candidate value in the predetermined posture and increase or reduce the input candidate value according to the inclination angle centering on the reference value.

APPLICATION EXAMPLE 4

In the input device according to the application example, it is preferable that the storing unit stores an upper limit value and a lower limit value of the inclination angle and an upper limit value and a lower limit value of the input candidate value, and, when the inclination angle is one of the upper limit value and the lower limit value, the candidate-value determining unit determines the input candidate value as one of the upper limit value and the lower limit value.

With such a configuration, it is possible to associate the upper and lower limit values of the inclination angle with the upper and lower limit values of the input candidate value.

APPLICATION EXAMPLE 5

In the input device according to the application example, it is preferable that the candidate-value determining unit increases a rate of change of the increase/decrease value according to an increase in the displacement amount.

With such a configuration, it is possible to quickly display the upper and lower limit values of the input candidate value.

APPLICATION EXAMPLE 6

In the input device according to the application example, it is preferable that the storing unit stores, as the reference value, the input value decided by the deciding unit.

With such a configuration, it is possible to set the reference value as the input value determined last time.

APPLICATION EXAMPLE 7

In the input device according to the application example, it is preferable that the input device includes a storing unit configured to store data selectable as the input candidate value, and the candidate-value determining unit determines the data as the input candidate value according to the inclination angle.

With such a configuration, it is possible to determine one data corresponding to the inclination angle as the input candidate value out of the data stored in the storing unit.

APPLICATION EXAMPLE 8

An information processing device according to this application example includes an information processing unit configured to perform predetermined information processing on the basis of the input value decided by the input device.

With such a configuration, it is possible to apply, to the information processing device, the input device with which it is possible to easily and quickly display a desired input candidate value by inclining the input device while visually recognizing the input candidate value.

APPLICATION EXAMPLE 9

An input method according to this application example includes: a detecting step for detecting body motion information concerning a limb; an inclination-angle calculating step for calculating an inclination angle of the limb on the basis of the body motion information; a display step for displaying an input candidate value corresponding to the inclination angle; and a deciding step for deciding the input candidate value as an input value.

With such a configuration, the body motion information of the limb is detected, the inclination angle is calculated from the detected body motion information, and the input candidate value is displayed according to the calculated inclination angle. Therefore, since the input candidate value is displayed according to the inclination angle, by inclining the input device while visually recognizing the input candidate value, it is possible to easily and quickly display a desired input candidate value and decide the desired input candidate value as the input value.

DESCRIPTION OF EMBODIMENTS

An embodiment of the present invention is explained below with reference to the drawings.

A preferred embodiment of the present invention is explained below with reference to the drawings. This embodiment is an embodiment in which an information processing device of the present invention is applied to a pulse meter of a wristwatch type. Note that it goes without saying that a mode applicable with the present invention is not limited to the embodiment explained below. For example, a form of the pulse meter is not limited to the wristwatch type. A form of a ring type can also be assumed.

1. Exterior Configuration

Figure 1:
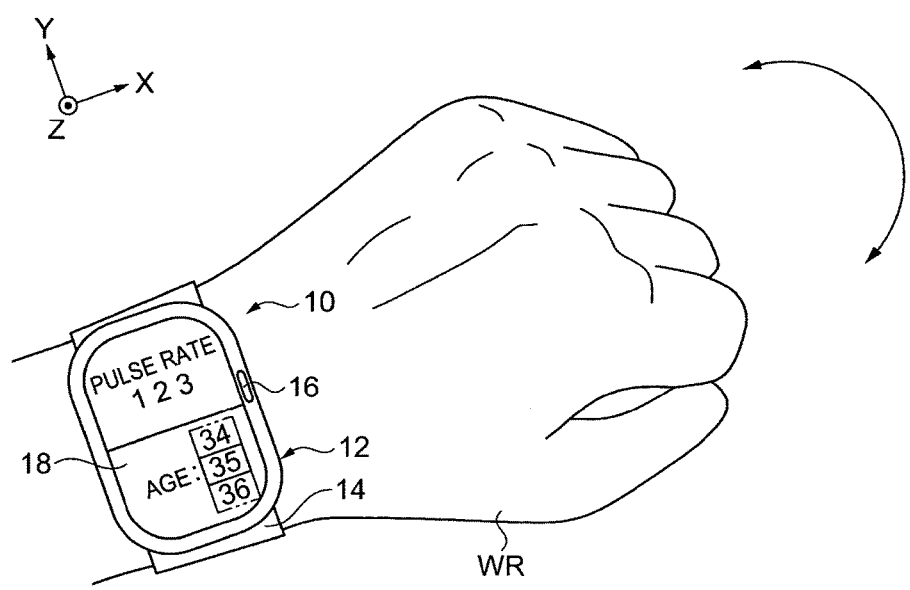
FIG. 1 is a diagram of a pulse meter according to an embodiment of the present invention worn on a wrist of a subject.

FIG. 1 is a diagram of a pulse meter 10 in this embodiment worn on a wrist WR, which is a limb, of a subject. The pulse meter 10 includes a wristband 14. On a case 12, an operation button 16 for operating the pulse meter 10 and a liquid crystal display panel 18 are disposed. The liquid crystal display panel 18 can display time, an operation state of the pulse meter 10, and various kinds of biological information (a pulse rate, the number of steps, a consumed calorie, etc) with characters, numbers, icons, and the like. Individual information (age, height, etc.) of the subject for calculating the various kinds of biological information can be input to the liquid crystal display panel 18.

On the back of the case 12, a pulse wave sensor 70 (FIG. 2) that detects a pulse wave of the subject and outputs a pulse wave signal is disposed. The pulse wave sensor 70 detects a pulse wave in the wrist WR of the subject. In this embodiment, the pulse wave sensor 70 is a photoelectric pulse wave sensor and includes a mechanism for optically detecting a pulse wave.

Note that, in the following explanation, a normal direction of a cover glass surface of the case 12, which is a direction positive on a display surface side, is represented as a Z axis, an up-down direction, which is positive in a direction toward a 12 o'clock direction of a clock, is represented as a Y axis, and a left-right direction, which is positive in a direction toward a 3 o'clock direction of the clock, is represented as an X axis.

In this embodiment, the subject turns the wrist WR wearing the pulse meter 10, that is, turns the wrist WR around the X axis, whereby age displayed on the liquid crystal display panel 18 increases or decreases according to a turning amount. The subject depresses the operation button 16 with a finger of the other hand, whereby age selection, which is one of input items, is decided.

Figure 2:
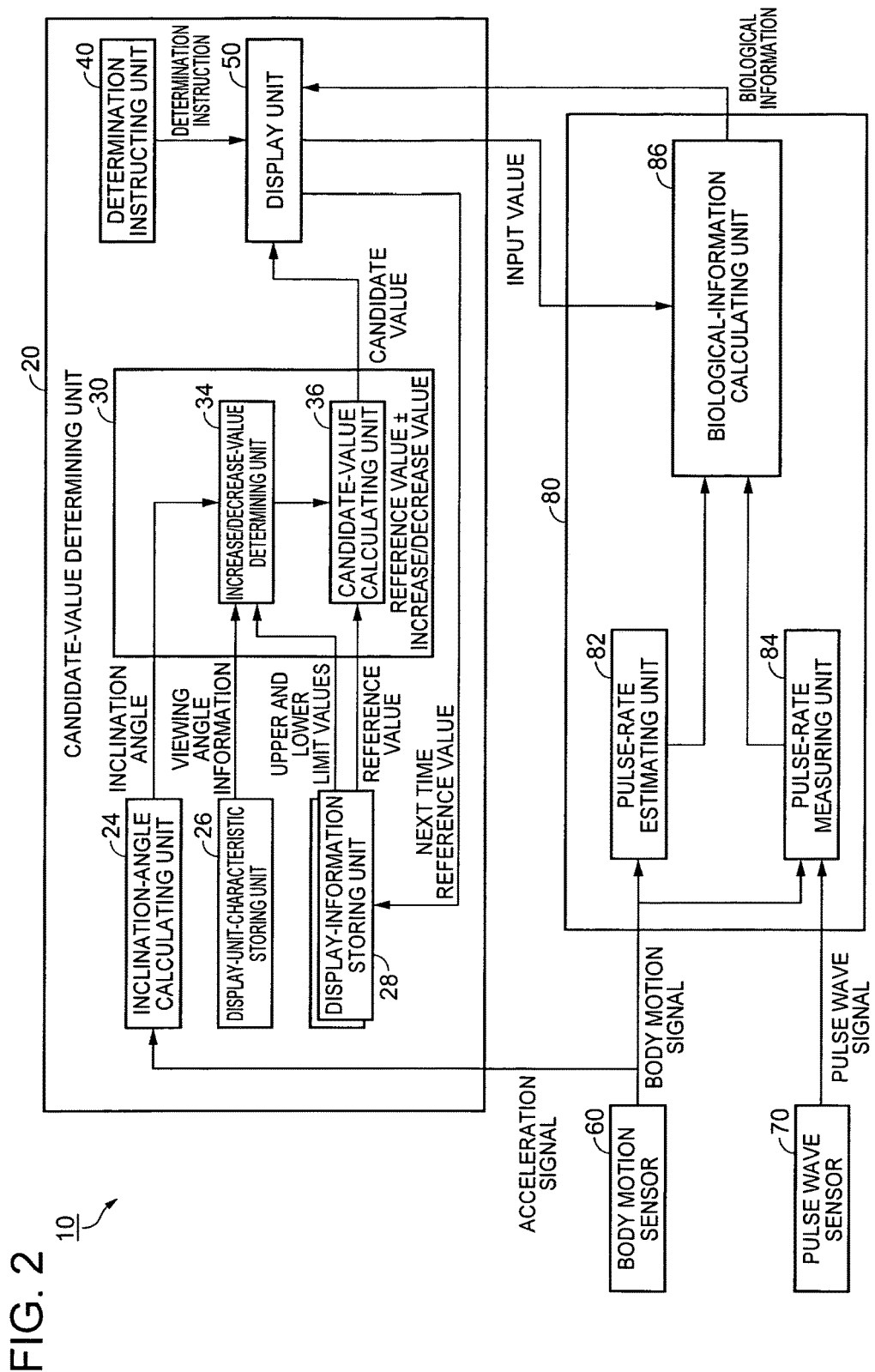
FIG. 2 is a diagram showing the functional configuration of the pulse meter according to the embodiment of the present invention.

FIG. 2 is a diagram showing the functional configuration of the pulse meter 10. The pulse meter 10 includes an input unit 20 for inputting individual information, a biological-information detecting unit 80 that detects biological information, a body motion sensor 60 that detects a body motion of the subject, and the pulse wave sensor 70 that detects a pulse wave. Note that, as the body motion sensor 60, a configuration including at least an acceleration sensor is assumed. However, a configuration including a gyro sensor can also be assumed.

The pulse meter 10 includes hardware such as a CPU, a ROM, a RAM, and a flash memory, all of which are not shown in the figure. The input unit 20 and the biological-information detecting unit 80 function when the hardware and software stored in the ROM or the like cooperate with each other.

1. Input Unit

The input unit 20 includes an inclination-angle calculating unit 24, a display-unit-characteristic storing unit 26, a display-information storing unit 28, a candidate-value determining unit 30, a determination instructing unit 40, and a display unit 50 and has a function of inputting individual information (age, height, etc.) of the subject. Note that, in explaining the function of the input unit 20, FIG. 3 for explaining the inclination of the pulse meter 10 is also referred to as appropriate. The input unit 20 is equivalent to the input device. The display-unit-characteristic storing unit 26 and the display-information storing unit 28 are equivalent to the storing unit.

The inclination-angle calculating unit 24 calculates an inclination angle of the pulse meter 10 on the basis of an acceleration signal obtained from the acceleration sensor included in the body motion sensor 60. Note that the body motion sensor 60 is equivalent to the body-motion-information detecting unit that detects body motion information of the wrist WR. In this embodiment, as the acceleration sensor, a three-axis acceleration sensor capable of detecting accelerations in three axis directions substantially orthogonal to one another is assumed. The detected body motion information is output to the input unit 20 and the biological-information detecting unit 80. The inclination-angle calculating unit 24 of the input unit 20 calculates, on the basis of an acceleration signal and a gravitational acceleration signal obtained from the three-axis acceleration sensor, an inclination angle in a direction of turning around the X axis. Note that an example of a calculation method is disclosed in, for example, JP-A-2012-105762. The body motion information input to the biological-information detecting unit 80 is used for processing for removing a body motion noise component signal from a pulse wave signal and extracting a beat component signal as explained below. In this way, in the input unit 20 and the biological-information detecting unit 80, the body motion information received from the body motion sensor 60 is used for different purposes. However, by configuring the pulse meter 10 to use a common body motion sensor 60, compared with when body motion sensors adapted to the respective purposes are used, it is possible to simplify the device configuration of the pulse meter 10 and realize a reduction in costs and a reduction in power consumption.

Figure 3:
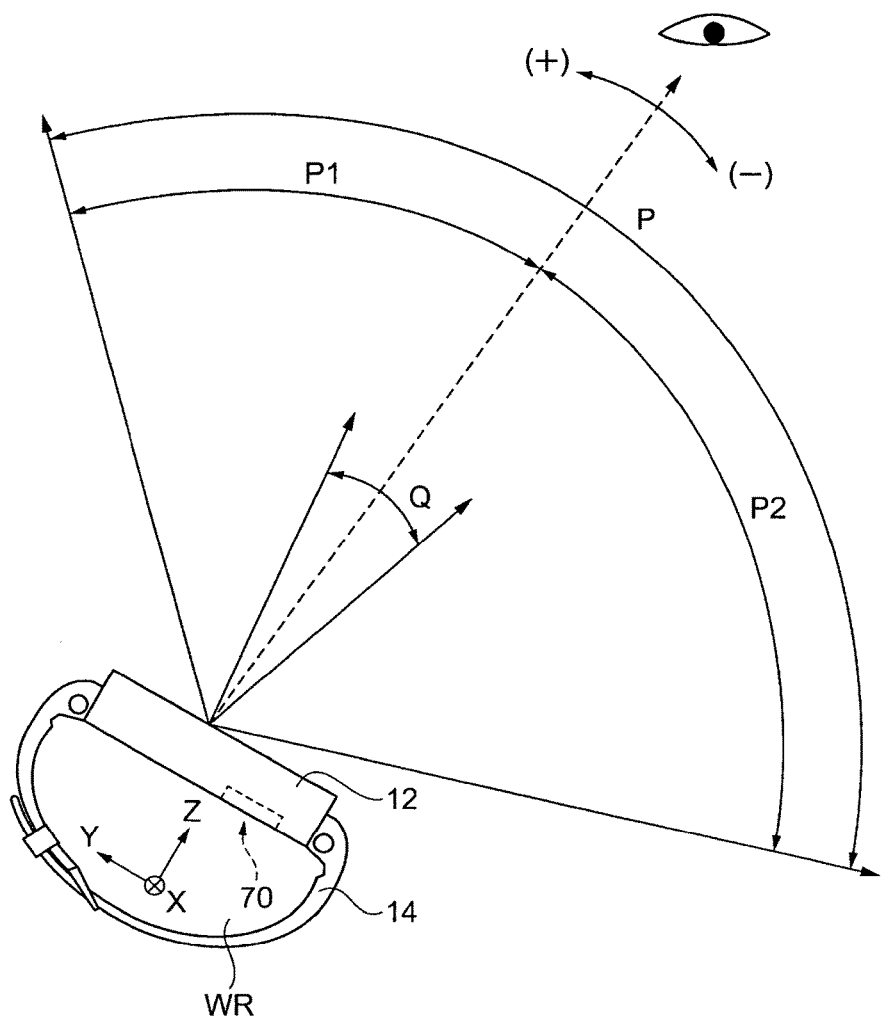
FIG. 3 is a diagram for explaining an inclination of the pulse meter according to the embodiment of the present invention.

In this embodiment, as shown in FIG. 3, a natural posture (a predetermined posture) in which the subject wears the pulse meter 10 on the wrist WR and can visually recognize the liquid crystal display panel 18 of the pulse meter 10 is set as a reference state. That is, the reference state is a state in which a normal vector (the Z axis) of a cover glass surface of the case 12 has a predetermined offset angle with respect to the gravitational acceleration direction. It is assumed that the offset angle is stored as a reference value in advance. The inclination-angle calculating unit 24 calculates, as inclination angle information, a relative inclination angle of the pulse meter 10 inclined when the wrist WR is turned in a (+) direction or a (−) direction from the reference state, that is, a displacement amount equivalent to a displacement angle from the reference value. The inclination angle information calculated by the inclination-angle calculating unit 24 is sent to the candidate-value determining unit 30.

Note that the reference state is not prevented from being assumed as, for example, a state in which a display surface of the pulse meter 10 is substantially horizontal. A state in which the pulse meter 10 is worn on the wrist WR and the pulse wave sensor 70 detects a pulse wave of the subject may be determined as the reference state. A form can also be assumed in which the subject operates the operation button 16 to explicitly determine the reference state. Information concerning the determined reference information may be stored in the display-information storing unit 28. Further, the reference state is the natural posture (the predetermined posture) in which the subject can visually recognize the liquid crystal display panel 18 of the pulse meter 10. However, the reference state is not limited to this. For example, the reference state may be determined on the basis of visibility and a positional relation with a limb of a predetermined part of the pulse meter 10 such as a logo or an LED (Light Emitting Diode) for notification to the user.

The display-unit-characteristic storing unit 26 stores visible viewing angle information of the liquid crystal display panel 18 equivalent to the display unit 50. In this embodiment, a total viewing angle of the liquid crystal display panel 18 is represented as P, a viewing angle in turning the wrist WR in the (+) direction is represented as P2, and a viewing angle in turning the wrist WR in the (−) direction is represented as P1. Note that, when a viewing angle is wide as in an organic EL panel, it is desirable to set a turnable angle of a standard wrist WR as P. That is, it is desirable to set the turnable angle to satisfy P≥P1+P2. P1 and P2 may be set to be the same angle or may be set to be angles different from each other. When P1 and P2 are set as P1=P2, when turning operation is performed from the reference state, display information displayed on the liquid crystal display panel 18 changes at the same rate irrespective of in which of the (±) direction and the (−) direction the wrist WR is turned. Therefore, the user can easily intuitively grasp how the display information changes when the wrist WR is turned to which degree.

On the other hand, when P1 and P2 are set as P1≠P2, a turnable angle in a direction in which the wrist WR can be easily turned according to a human body characteristic may be set large, that is, P1 and P2 may be set as P1>P2. By setting the angles in this way, a turnable angle in a direction in which the wrist WR easily turns, that is, a direction in which the liquid crystal display panel 18 moves away from the human body is set large. Therefore, operational feeling of the user is improved. The viewing angle information stored by the display-unit-characteristic storing unit 26 is referred to from the candidate-value determining unit 30.

The display-information storing unit 28 stores, for each kind of individual information such as age, height, and weight, upper and lower limit values and a reference value first displayed as a candidate value. The display-information storing unit 28 has a function of storing a determined input value as a reference value of the next time. Therefore, when the pulse meter 10 is in an initial state, a predetermined value stored in advance is the reference value. Thereafter, an input value determined the last time is the reference value.

1.1 Candidate-Value Determining Unit

The candidate-value determining unit 30 includes an increase/decrease-value determining unit 34 and a candidate-value calculating unit 36.

The increase/decrease-value determining unit 34 determines, according to the inclination angle calculated by the inclination-angle calculating unit 24, an increase/decrease value to be added to or subtracted from the reference value. In this embodiment, the increase/decrease-value determining unit 34 refers to the viewing angle information received from the display-unit-characteristic storing unit 26 and refers to the upper and lower limit values of the individual information received from the display-information storing unit 28. The increase/decrease-value determining unit 34 determines the increase/decrease value such that the inclination angle is the upper and lower limit values of the individual information at both ends of the total viewing angle P, that is, the inclination angle is the upper limit value of the individual information in the case of P2 and is the lower limit value of the individual information in the case of P1 and, in addition, a rate of change of the increase/decrease value increases in proportion to a difference between the inclination angle and a reference angle. The increase/decrease value determined by the increase/decrease-value determining unit 34 is sent to the candidate-value calculating unit 36. Note that the rate of change of the increase/decrease value may be nonlinearly changed according to the difference between the inclination angle and the reference angle. The increase/decrease-value determining unit 34 may be configured such that the rate of change corresponding to the inclination angle is different according to a direction of a turning motion. By configuring the pulse meter 10 in this way, the rate of change is set to be large when the wrist WR is turned in the (−) direction in which the turning motion is relatively more difficult than in the (+) direction in which the turning motion can be relatively easily performed, that is, when turning operation is performed in a direction in which the body is brought close to the Z axis. Consequently, operability of the user is improved.

For example, when the inclination angle increases from 0 degree to 10 degrees, the increase/decrease value is +5 units. When the inclination angle increases from 30 degrees to 40 degrees, the increase/decrease value is +10 units. When P2 is 60 degrees, the increase/decrease value is 0 unit when the inclination angle exceeds 60 degrees.

Note that a form can also be assumed in which a predetermined angle (Q) of approximately 5 degrees is determined in advance as an idle angle and, when the inclination angle is equal to or smaller than the predetermined angle (Q), the increase/decrease-value determining unit 34 maintains the reference value or the latest updated value.

The candidate-value calculating unit 36 performs an arithmetic operation of the reference value stored by the display-information storing unit 28 and the increase/decrease value determined by the increase/decrease-value determining unit 34 and calculates a candidate value (an input candidate value). The calculated candidate value is sent to the display unit 50 and displayed.

The subject depresses an operation button 16 equivalent to the determination instructing unit 40 or taps the case 12, whereby the candidate value is decided as an input value. The decided input value is sent to the biological-information detecting unit 80. Note that the determination instructing unit 40 is equivalent to the deciding unit.

Note that the candidate value is not limited to numerical data. A form can also be assumed in which one of a plurality of text data and image data is set as the candidate value. For example, when an input item is "meal content", text data and image data corresponding to "bread", "rice", "noodles", and the like are displayed to be selectable as the candidate value according to the inclination angle. In this case, the selectable text data and image data are stored in the display-information storing unit 28 to be editable.

In this embodiment, input target individual information is determined according to biological information to be displayed. However, the input target individual information may be explicitly selected from the input unit 20. For example, candidates of input items such as "age", "sex", "weight", and "height" are sequentially selectably displayed according to the inclination angle. After selecting a desired input item, the subject may select a candidate value of the selected input item.

2. Biological-Information Detecting Unit

The biological-information detecting unit 80 includes a pulse-rate estimating unit 82, a pulse-rate measuring unit 84, and a biological-information calculating unit 86. The biological-information detecting unit 80 calculates biological information of the subject on the basis of a body motion signal obtained from the body motion sensor 60 and a pulse wave signal obtained from the pulse wave sensor 70. In this embodiment, as biological information to be detected, a pulse rate, the number of steps, and a consumed calorie of the subject are assumed. However, the biological information is not limited to these. For example, a blood pressure of the subject, detection of an irregular pulse, and the like can also be assumed.

2.1. Pulse Wave Sensor

Figure 4:
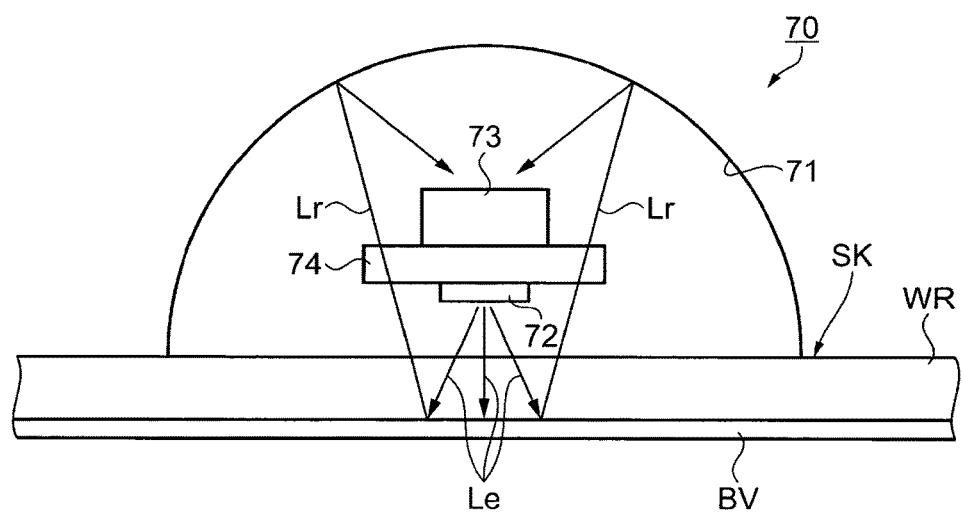
FIG. 4 is a diagram showing the operation of a pulse sensor.

In this embodiment, the pulse wave sensor 70 is a photoelectric pulse wave sensor and includes a mechanism for optically detecting a pulse wave. FIG. 4 is a diagram showing the operation of the pulse wave sensor 70 and is an enlarged view of the internal structure of the pulse wave sensor 70 viewed from a side surface. Note that members in FIG. 4 are shown with scales varied for each of the members to show the members in sizes recognizable on the drawing.

The pulse wave sensor 70 is set in a hemispherical housing space having a circular bottom surface formed on the back side of the case 12. In the housing space, a light source 72 such as an LED and a light receiving element 73 such as a phototransistor are incorporated. The inner surface of the hemisphere is a mirror surface 71. When the bottom surface side of the hemisphere is set as the downward direction, the light receiving element 73 and the light source 72 are respectively mounted on the upper surface and the lower surface of a substrate 74.

When light Le is irradiated toward a skin SK of the wrist WR of the user by the light source 72, the irradiated light Le is reflected on a blood vessel BV under the skin and returns into the hemisphere as reflected light Lr. The reflected light Lr is further reflected on the hemispherical mirror surface 71 and made incident on the light receiving element 73 from the upward direction.

The intensity of the reflected light Lr reflected from the blood vessel BV fluctuates reflecting fluctuation in a blood flow according to light absorbing action of hemoglobin in blood. The pulse wave sensor 70 causes the light source 72 to blink at a predetermined cycle shorter than a cycle of a beat. The light receiving element 73 outputs a pulse wave signal corresponding to light reception intensity through photoelectric conversion in every lighting opportunity of the light source 72.

2.2. Pulse-Rate Measuring Unit

The pulse-rate measuring unit 84 measures a pulse rate on the basis of a pulse wave signal detected by the pulse wave sensor 70. The pulse wave signal is a signal obtained by superimposing a beat component signal and a body motion noise component signal of the subject. Therefore, the pulse meter 10 removes the body noise component signal from the pulse wave signal on the basis of a body motion signal output from the body motion sensor 60 and extracts the beat component signal. The pulse meter 10 measures a pulse rate on the basis of the extracted beat component signal.

Specifically, for example, a digital filter such as an FIR (Finite Impulse Response) filter is configured as an adaptive filter. The pulse meter 10 executes, using the adaptive filter, processing for removing a body motion noise component from the pulse wave signal as digital signal processing. The pulse meter 10 applies a frequency analysis to the extracted beat component signal to specify a beat presentation spectrum and measures a pulse rate on the basis of a frequency (or a cycle) of the beat presentation spectrum. As the frequency analysis, for example, fast Fourier transform (FFT) can be applied.

2.3. Pulse-Rate Estimating Unit

The pulse-rate estimating unit 82 calculates a pitch (a pace) of the subject from acceleration detected by the acceleration sensor to calculate exercise intensity of the subject. The calculation of the pitch can be performed by applying a predetermined frequency analysis (e.g., FFT) to an acceleration signal output from the acceleration sensor and specifying and extracting a frequency component equivalent to the pitch. Details of the calculation method are disclosed in, for example, JP-A-2004-81745.

Subsequently, the pulse-rate estimating unit 82 estimates a pulse rate from the pitch on the basis of a correspondence relation between the pitch and the pulse rate set in advance. In this embodiment, a beat estimation formula indicating a correlation between the pitch and the pulse rate may be stored in advance and the pulse rate may be estimated by applying the pitch to the beat estimation formula. A table indicating the correlation between the pitch and the pulse rate may be stored in advance and the pulse rate corresponding to the pitch may be estimated with reference to the table.

2.4. Biological-Information Calculating Unit

The biological-information calculating unit 86 determines a pulse rate of the subject from the pulse rate estimated by the pulse-rate estimating unit 82 or the pulse rate measured by the pulse-rate measuring unit 84 and calculates the number of steps and a consumed calorie on the basis of an input value input by the input unit 20 and the pitch and the pulse rate. Various kinds of biological information calculated by the biological-information calculating unit 86 is sent to the display unit 50 and displayed.

The biological-information calculating unit 86 determines the pulse rate on the basis of a state of the subject and a pulse wave signal. For example, when determining on the basis of the pitch and the pulse wave signal that the subject is in a stable state and determining that a ratio of a signal component and a noise component included in the pulse wave signal satisfies a predetermined standard, the biological-information calculating unit 86 adopts the pulse rate measured by the pulse-rate measuring unit 84 as the pulse rate of the subject. On the other hand, when determining that the ratio of the signal component and the noise component included in the pulse wave signal does not satisfy the predetermined standard, the biological-information calculating unit 86 adopts the pulse rate estimated by the pulse-rate estimating unit 82 as the pulse rate of the subject. When determining that the subject shifts from a walking state to a running state or shifts from the running state to the walking state, the biological-information calculating unit 86 estimates a pulse rate in a transient state on the basis of the pulse rate estimated by the pulse-rate estimating unit 82. As a procedure for determining the pulse rate of the subject, for example, the procedure disclosed in JP-A-2012-232010 can be adopted.

As a method of calculating a consumed calorie from the measured pulse rate, a method of calculating, taking into account the fact that oxygen is always used during energy consumption, an oxygen intake amount from the pulse rate and calculating the consumed calorie from the oxygen intake amount can be adopted. Details concerning the method are disclosed in, for example, JP-A-2009-195589.

Figure 5:
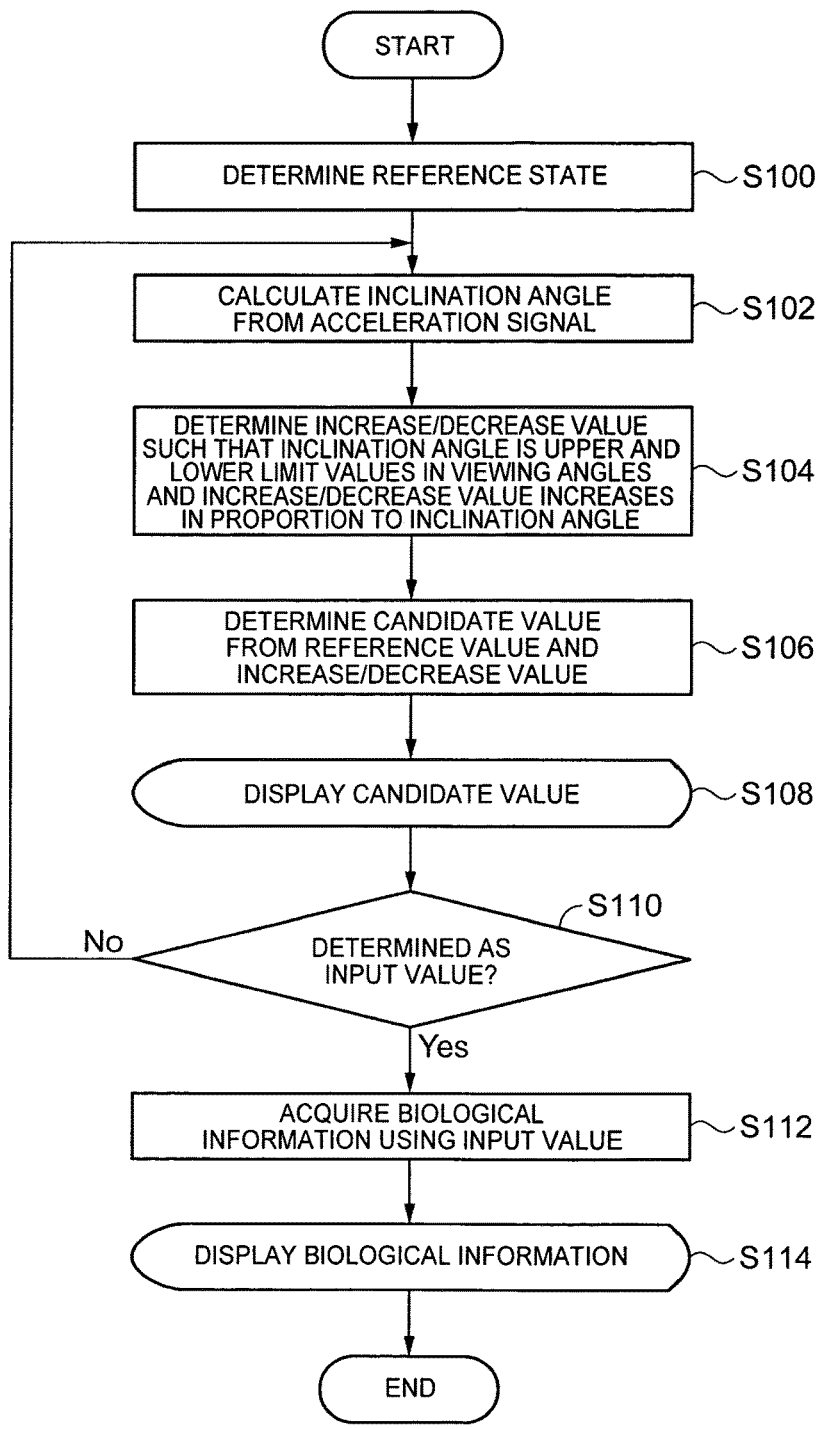
FIG. 5 is a flowchart for explaining a flow of processing in which the pulse meter according to the embodiment of the present invention acquires biological information.

FIG. 5 is a flowchart for explaining a flow of processing in which the pulse meter 10 acquires biological information. First, the pulse meter 10 determines a reference state serving as a reference of an inclination angle (step S100).

Subsequently, the acceleration sensor detects an acceleration signal <a detecting step>. The pulse meter 10 calculates, on the basis of the detected acceleration signal, the inclination angle based on the reference state (step S102) <an inclination-angle calculating step>.

Subsequently, the pulse meter 10 determines an increase/decrease value corresponding to the inclination angle such that the inclination angle is upper and lower limit values respectively in the viewing angles (P1 and P2) and the increase/decrease value increases in proportion to the inclination angle (step S104).

Subsequently, the pulse meter 10 determines a candidate value from a reference value corresponding to individual information and the increase/decrease value (step S106) <a candidate-value determining step> and displays the determined candidate value (step S108) <a display step>.

Subsequently, the pulse meter 10 determines whether the candidate value is decided as an input value (step S110). When determining that the candidate value is not decided as the input value (No in step S110), the pulse meter 10 returns to step S102.

On the other hand, when determining that the candidate value is decided as the input value (Yes in step S110) <a deciding step>, the pulse meter 10 acquires biological information using the input value (step S112).

Subsequently, the pulse meter 10 displays the acquired biological information (step S114) and ends the series of processing.

According to the embodiment explained above, effects explained below are attained.

(1) Since the pulse meter 10 is worn on the wrist WR and tilted with the wrist WR as an axis, it is possible to display a candidate value of individual information such as age or height according to an inclination angle and determine the displayed candidate value as an input value. Therefore, it is possible to easily and quickly determine a desired numerical value out of numerical data in a wide selectable range.

(2) The number of buttons operated to select the candidate value of the individual information can be reduced. Therefore, it is possible to reduce manufacturing costs of the pulse meter 10. In addition, it is possible to expand a display region of the pulse meter 10.

(3) The acceleration sensor for estimating a pulse rate in the biological-information detecting unit 80 is also used for detecting an inclination angle by the turning of the wrist WR. Therefore, since one device is effectively used, it is possible to attain a reduction in the costs of the pulse meter 10.

The present invention is explained above on the basis of the embodiment shown in the figures. However, the present invention is not limited to this embodiment. Modifications explained below can also be assumed.

(1) In this embodiment, the inclination angle by the turning of the wrist WR, that is, turning around the X axis is set as the detection target. However, inclination angles by turning around the Y axis and the Z axis may be set as the detection target. Further, a form can also be assumed in which the detection target of the inclination angle is two or more axes and individual information is respectively allocated to the respective axes.

(2) The increase/decrease-value determining unit 34 determines the increase/decrease value to increase in proportion to the difference between the inclination angle and the reference angle. However, a form can also be assumed in which the increase/decrease value per inclination angle is fixed such that the increase/decrease value increases by 5 units every time the inclination angle increases 10 degrees. Further, a form can also be assumed in which the increase/ decrease value increases or decreases by 1 unit at every predetermined time such that the increase/decrease value increases by +5 units when the pulse meter 10 is tilted in the (+) direction for 5 seconds.

(3) The increase/decrease value is 0 unit when the inclination angle exceeds the total viewing angle P. However, in addition, a form can also be assumed in which the inclination angle exceeding the total viewing angle P is notified to the subject by an alarm, vibration, or blinking of a lamp.

(4) The decision of the candidate value is not limited to the depression of the operation button 16. For example, a form can also be assumed in which the pulse meter 10 includes sound recognition means, image recognition means, a motion sensor, or the like and decides the candidate value according to voice of the subject, motions of the face and the eyes of the subject, or a motion of the wrist WR of the subject.

(5) The input value determined by the input unit 20 is not limitedly sent to the biological-information detecting unit 80 that processes biological information. The input value may be sent to various information processing devices including a personal computer. The present invention is not limited to the form in which the input unit 20 and the information processing device (the information processing unit) that processes information on the basis of an input value to the input unit 20 are integrated. For example, a form can also be assumed in which the input device including the input unit 20 and the information processing device are separately configured and the input value is transmitted from the input device worn on a limb to the information processing device through radio communication.

(6) The increase/decrease-value determining unit 34 sets the inclination angle as the upper limit value of the individual information when the inclination angle is P2 and sets the inclination angle as the lower limit value of the individual information when the inclination angle is P1. However, the increase/decrease-value determining unit 34 is not limited to this. The increase/decrease-value determining unit 34 may be configured to associate desired individual information with the inclination angles P1 and P2. Further, the increase/decrease-value determining unit 34 may be configured to set individual information corresponding to the reference state and an increase/decrease value (a rate of change) corresponding to a displacement amount from the reference state and enable the candidate calculating unit 36 to limitlessly select the candidate value on the basis of a motion of the user. Note that the configuration does not deny the setting of the upper limit value and the lower limit value of the individual information. It is also possible to attain improvement of convenience for the user by setting the upper limit value and the lower limit value for convenience.

The components and the combinations of the components in the embodiments are examples. Addition, omission, substitution, and other changes of the components are possible within a range not departing from the spirit of the present invention. The present invention is not limited by the embodiments and is limited only by the scope of claims.

REFERENCE SIGNS LIST

10 Pulse meter
12 Case
14 Wristband
16 Operation button
18 Liquid crystal display panel
20 Input unit
24 Inclination-angle calculating unit
26 Display-unit-characteristic storing unit
28 Display-information storing unit
30 Candidate-value determining unit
34 Increase/decrease-value determining unit
36 Candidate-value calculating unit
40 Determination instructing unit
50 Display unit
60 Body motion sensor
70 Pulse wave sensor
71 Mirror surface
72 Light source
73 Light receiving element
74 Substrate
80 Biological-information detecting unit
82 Pulse-rate estimating unit
84 Pulse-rate measuring unit
86 Biological-information calculating unit

What is claimed is:

1. An input device comprising:
a case configured to be worn on the wrist of a user:
a body-motion-information detecting unit configured to detect body motion information concerning the wrist;
an inclination-angle calculating unit configured to calculate an inclination angle of the limb wrist on the basis of the body motion information;
a candidate-value determining unit configured to determine an input candidate value, from a plurality of displayed data selectable as the input candidate value, by changing the input candidate value from a first input candidate value to a second input candidate value using the calculated inclination angle, wherein the first and second input candidate values correspond to individual information about the user used for calculating biological information relating to the user:
a display unit configured to change a display portion displaying the first input candidate value to the second input candidate value in response to the second input candidate value being the determined input candidate value; and
a setting unit configured to receive a user input while the determined input candidate value is displayed on the display portion and set the determined input candidate value as an input value in response to receiving the user input, wherein the user input is one of a depression of a button or a tap on a case housing the input device,
wherein the body-motion-information detecting unit, the inclination-angle calculating unit, the candidate-value determining unit, the display unit, and the setting unit are housed within the case.

2. The input device according to claim 1, wherein
the body-motion-information detecting unit includes an acceleration sensor configured to output an acceleration signal, and
the inclination-angle calculating unit calculates a displacement amount from the inclination angle in a predetermined posture of the limb on the basis of the acceleration signal.

3. The input device according to claim 2, further comprising:
a storing unit configured to store the first input candidate value in the predetermined posture as a reference value, wherein
the candidate-value determining unit determines an increase/decrease value on the basis of the inclination angle and calculates the second input candidate value using the reference value and the increase/decrease value.

4. The input device according to claim 3, wherein
the storing unit stores an upper limit value and a lower limit value of the inclination angle and an upper limit value and a lower limit value of the input candidate value, and
when the inclination angle is one of the upper limit value and the lower limit value, the candidate-value determining unit determines the input candidate value as one of the upper limit value and the lower limit value.

5. The input device according to claim 3, wherein the candidate-value determining unit increases a rate of change of the increase/decrease value according to an increase in the displacement amount.

6. The input device according to claim 3, wherein the storing unit stores, as the reference value, the input value decided by the deciding unit.

7. The input device according to claim 1, comprising a storing unit configured store data selectable as the input candidate value.

8. An information processing device comprising:
the input device according to claim 1; and
an information processing unit configured to perform predetermined information processing on the basis of the input value decided by the input device.

9. The input device according to claim 5, wherein the candidate-value determining unit is configured to determine the rate of change of the increase/decrease value based on a direction of a turning motion of the limb.

10. An input method comprising:
a detecting step for detecting body motion information concerning a wrist of a user;
a first display step for displaying a first input candidate value, from a plurality of displayed data selectable as an input candidate value;
an inclination-angle calculating step for calculating an inclination angle of the wrist limb, while the first input candidate value is displayed, on the basis of the body motion information;
a candidate value determining step for determining a second input candidate value, different from the first input candidate value, from the plurality of displayed data selectable as the input candidate value, using the calculated inclination angle, wherein the first and second input candidate values correspond to individual information about the user used for calculating biological information relating to the user;
a second display step for displaying the determined second input candidate value; and
a setting step for setting the determined second input candidate value as an input value in response to receiving a user input while the determined second input candidate value is displayed.

11. An input device comprising:
a body-motion-information detecting unit configured to detect body motion information concerning a limb;
an inclination-angle calculating unit configured to calculate an inclination angle of the limb on the basis of the body motion information;
a candidate-value determining unit configured to determine an input candidate value, from a plurality of displayed data selectable as the input candidate value, by changing the input candidate value from a first input candidate value to a second input candidate value using the calculated inclination angle;
a display unit configured to change a display portion displaying the first input candidate value to the second input candidate value in response to the second input candidate value being the determined input candidate value; and
a setting unit configured to receive a user input while the determined input candidate value is displayed on the display portion and set the determined input candidate value as an input value in response to receiving the user input, wherein the user input is one of a depression of a button or a tap on a case housing the input device,
wherein the body-motion-information detecting unit includes an acceleration sensor configured to output an acceleration signal, and the inclination-angle calculating unit calculates a displacement amount from the inclination angle in a predetermined posture of the limb on the basis of the acceleration signal,
where the input device further comprises a storing unit configured to store the first input candidate value in the predetermined posture as a reference value,
wherein the candidate-value determining unit determines an increase/decrease value on the basis of the inclination angle and calculates the second input candidate value using the reference value and the increase/decrease value, and
wherein the candidate-value determining unit increases a rate of change of the increase/decrease value according to an increase in the displacement amount.

* * * * *